United States Patent
Wang et al.

(10) Patent No.: US 10,925,552 B2
(45) Date of Patent: Feb. 23, 2021

(54) CBCT IMAGING SYSTEM WITH CURVED DETECTOR

(71) Applicant: CARESTREAM HEALTH, INC., Rochester, NY (US)

(72) Inventors: Xiaohui Wang, Pittsford, NY (US); David H. Foos, Webster, NY (US); Timothy J. Wojcik, Rochester, NY (US); Craig F. Hofmann, Fairport, NY (US)

(73) Assignee: Carestream Health, Inc., Rochester, NY (US)

( * ) Notice: Subject to any disclaimer, the term of this patent is extended or adjusted under 35 U.S.C. 154(b) by 0 days.

(21) Appl. No.: 16/083,017

(22) PCT Filed: Mar. 22, 2017

(86) PCT No.: PCT/US2017/023534
§ 371 (c)(1),
(2) Date: Sep. 7, 2018

(87) PCT Pub. No.: WO2017/165487
PCT Pub. Date: Sep. 28, 2017

(65) Prior Publication Data
US 2019/0083050 A1      Mar. 21, 2019

Related U.S. Application Data

(60) Provisional application No. 62/313,274, filed on Mar. 25, 2016.

(51) Int. Cl.
*H05G 1/02* (2006.01)
*A61B 6/03* (2006.01)
(Continued)

(52) U.S. Cl.
CPC .............. *A61B 6/035* (2013.01); *A61B 6/032* (2013.01); *A61B 6/04* (2013.01); *A61B 6/4007* (2013.01);
(Continued)

(58) Field of Classification Search
CPC ......... A61B 6/035; A61B 6/04; A61B 6/4007; A61B 6/4085; A61B 6/4266;
(Continued)

(56) References Cited

U.S. PATENT DOCUMENTS 4,400,820 A * 8/1983 O'Dell ................. A61B 6/0421
128/845
6,199,233 B1 3/2001 Kantrowitz et al.
(Continued)

FOREIGN PATENT DOCUMENTS

JP      2004-089571     3/2004

OTHER PUBLICATIONS

International Search Report dated Jun. 2, 2017 for International Application No. PCT/US2017/023534, 3 pages.

*Primary Examiner* — Kiho Kim

(57) ABSTRACT

A mobile CBCT imaging system is constructed on a mobile base. A scanning ring having an x-ray source and one or more curved detectors is connected to the mobile base. The scanning ring is configured to be spatially positioned as desired by an operator. The source is configured to revolve about an imaging axis and to emit radiographic energy toward the imaging axis, and the one or more detectors has an array of photosensors disposed along a curved surface facing the imaging axis.

19 Claims, 15 Drawing Sheets

(51) Int. Cl.
*A61B 6/04* (2006.01)
*A61B 6/00* (2006.01)

(52) U.S. Cl.
CPC .......... *A61B 6/4085* (2013.01); *A61B 6/4266* (2013.01); *A61B 6/4275* (2013.01); *A61B 6/4405* (2013.01); *A61B 6/4435* (2013.01); *A61B 6/4458* (2013.01); *A61B 6/4476* (2013.01); *A61B 6/501* (2013.01); *A61B 6/4447* (2013.01)

(58) Field of Classification Search
CPC ... A61B 6/4275; A61B 6/4405; A61B 6/4458; A61B 6/4476; A61B 6/501; A61B 6/4447; A61B 6/032; A61B 6/4435
See application file for complete search history.

(56) References Cited

U.S. PATENT DOCUMENTS

| | | | |
|---|---|---|---|
| 2003/0002626 A1* | 1/2003 | Hoheisel | A61B 6/032 378/98.8 |
| 2004/0022350 A1 | 2/2004 | Gregerson et al. | |
| 2005/0135560 A1* | 6/2005 | Dafni | A61B 6/56 378/101 |
| 2006/0222143 A1 | 10/2006 | Du | |
| 2007/0211863 A1* | 9/2007 | Graumann | A61B 6/4441 378/197 |
| 2008/0013691 A1* | 1/2008 | Gregerson | A61B 6/02 378/198 |
| 2008/0123819 A1 | 5/2008 | Jensen et al. | |
| 2008/0178893 A1* | 7/2008 | Kusner | A61B 6/0421 128/845 |
| 2009/0232272 A1 | 9/2009 | Tsujii et al. | |
| 2010/0246753 A1 | 9/2010 | Mollov | |
| 2011/0075794 A1* | 3/2011 | Boese | A61B 6/025 378/9 |
| 2011/0075809 A1* | 3/2011 | Boese | A61B 6/4014 378/92 |
| 2011/0228901 A1 | 9/2011 | Yorkston et al. | |
| 2011/0274238 A1* | 11/2011 | Maschke | A61B 6/035 378/9 |
| 2011/0315884 A1 | 12/2011 | Worstell et al. | |
| 2012/0106696 A1 | 5/2012 | Dafni | |
| 2012/0324648 A1* | 12/2012 | Amano | A61B 6/0375/601 |
| 2013/0074263 A1 | 3/2013 | Driemel et al. | |
| 2015/0049856 A1* | 2/2015 | Ritschl | A61B 6/4078 378/14 |
| 2015/0131775 A1 | 5/2015 | Yorkston et al. | |
| 2016/0038109 A1* | 2/2016 | Fortuna | A61B 6/4447 378/64 |
| 2016/0128653 A1* | 5/2016 | Fortuna | A61B 6/035 378/12 |

* cited by examiner

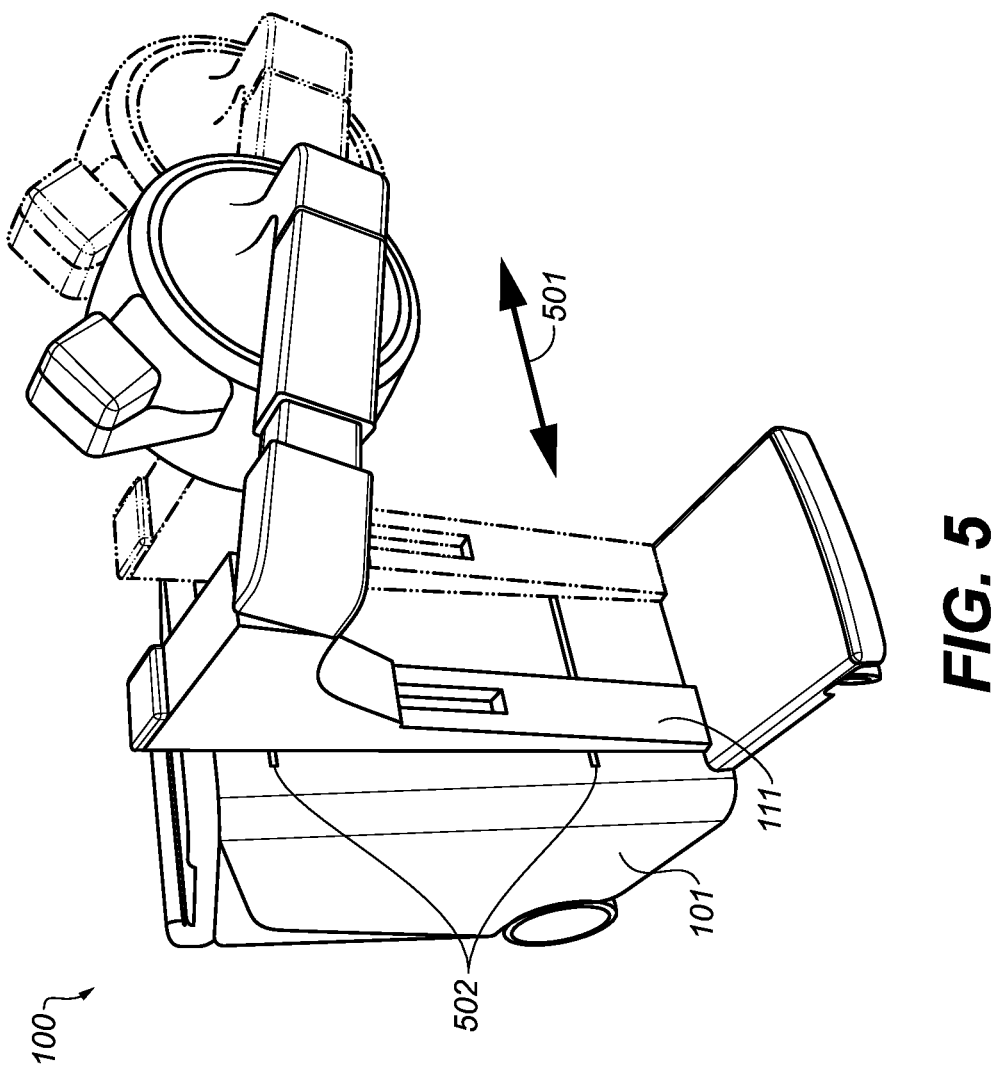

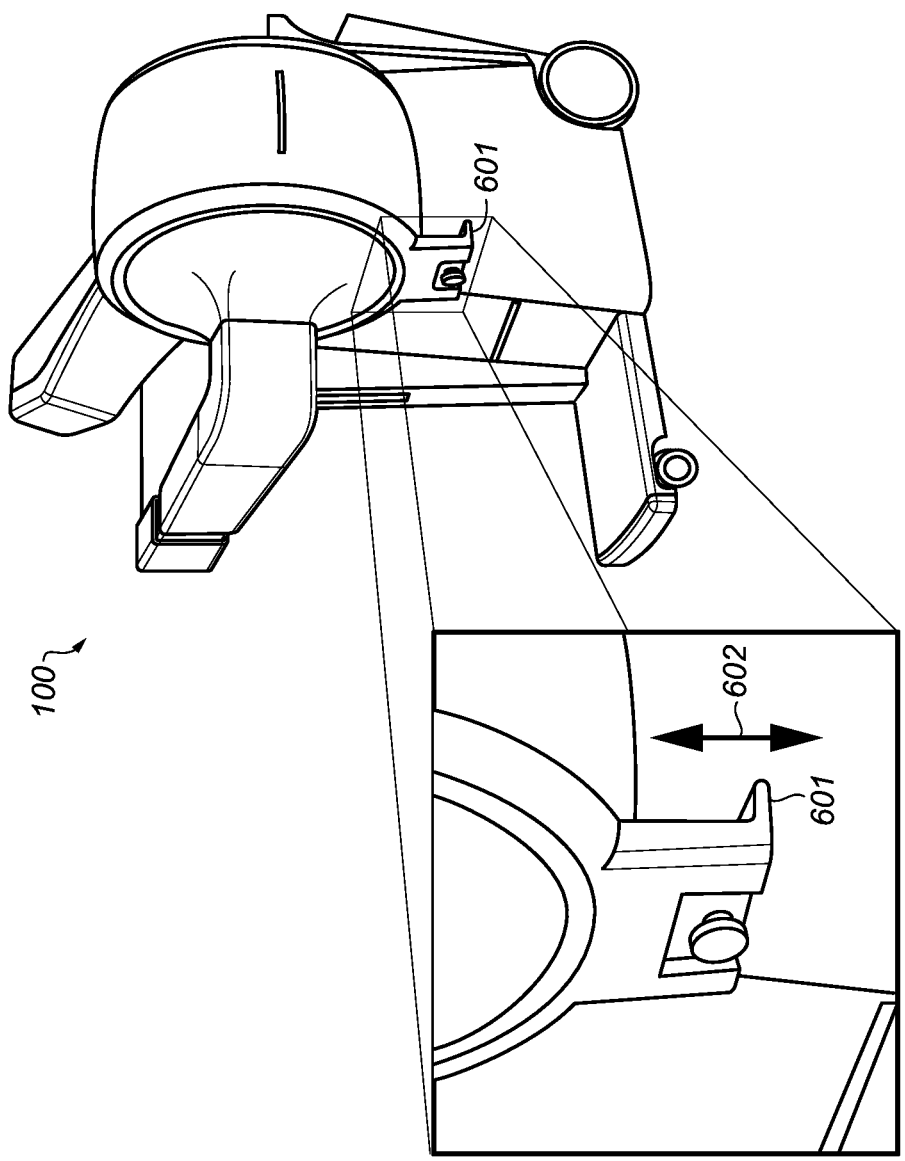

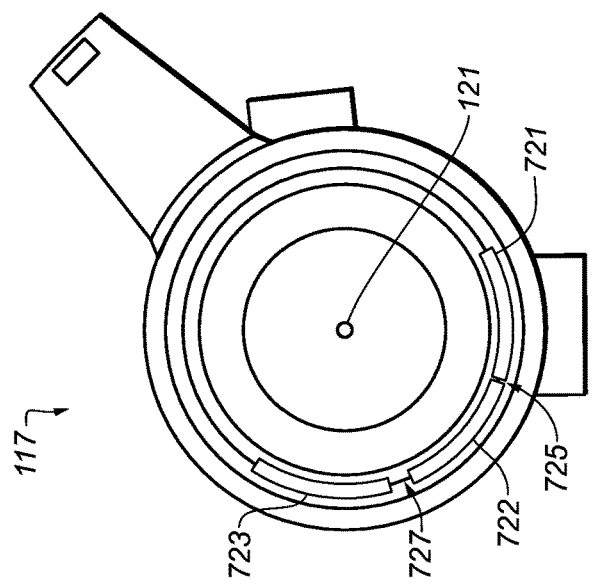
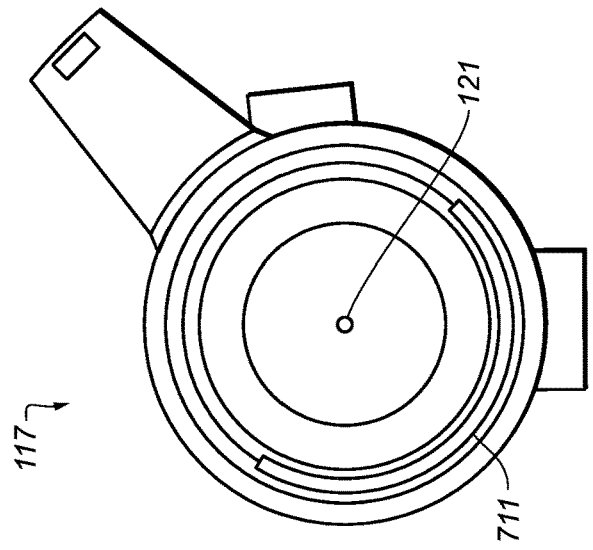
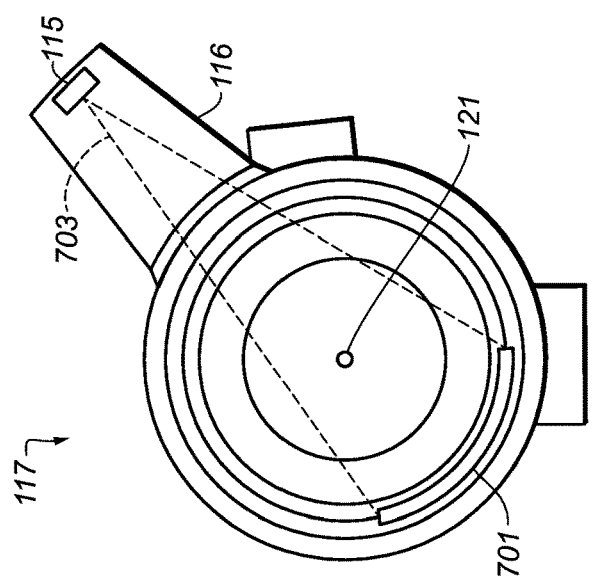

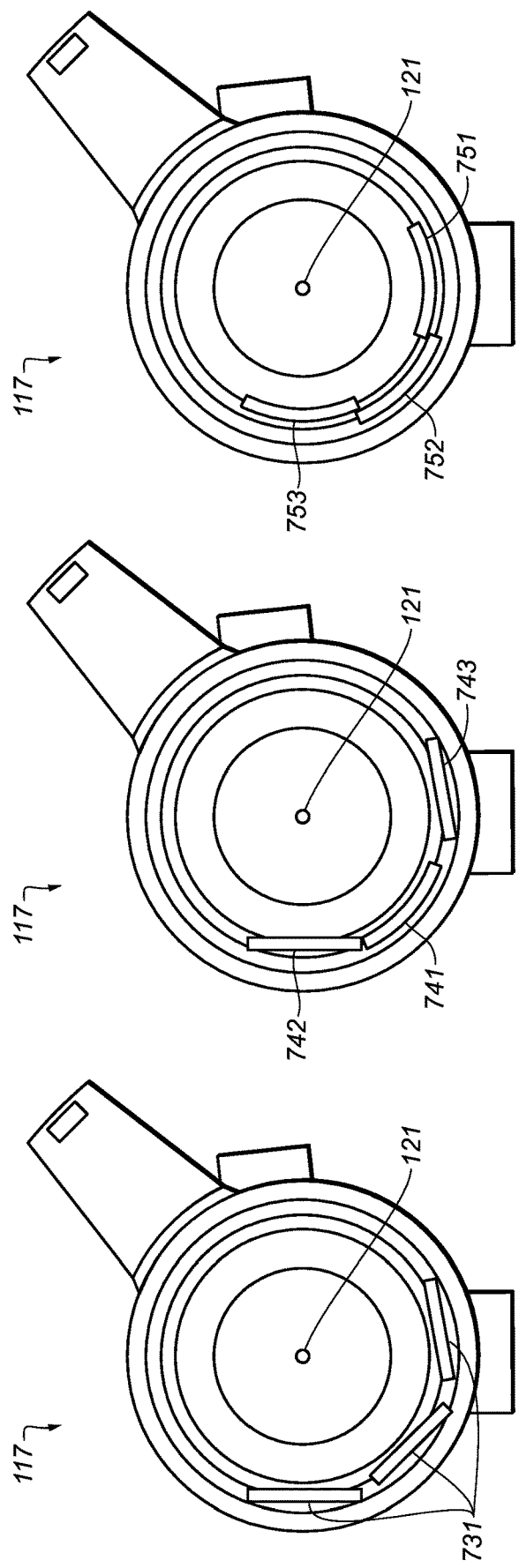

CBCT IMAGING SYSTEM WITH CURVED DETECTOR

CROSS REFERENCE TO RELATED APPLICATIONS

This application claims the benefit of and is a U.S. National Phase filing of PCT Application PCT/US2017/023534 filed Mar. 22, 2017 entitled "CBCT IMAGING SYSTEM WITH CURVED DETECTOR", in the name of Wang et al., which claims benefit of U.S. Provisional application U.S. Ser. No. 62/313,274, provisionally filed on Mar. 25, 2016, entitled "CBCT IMAGING SYSTEM WITH CURVED DETECTOR", in the name of Wang et al, all of which are incorporated herein in their entirety.

BACKGROUND OF THE INVENTION

The subject matter disclosed herein relates to a mobile radiographic imaging apparatus for head and neck radiographic imaging. In particular, one embodiment disclosed herein pertains to a mobile cone beam computed tomography imaging system.

BRIEF DESCRIPTION OF THE INVENTION

A mobile CBCT imaging system is constructed on a wheeled mobile base configured to be rolled over a surface. A scanning ring having an x-ray source and a curved detector is connected to the mobile base. A spatially positionable, adjustable arm is mechanically connected to the scanning ring and to the mobile base. The scanning ring is configured to be spatially positioned manually, as desired, by an operator. The source is positioned on one side of the scanning ring and is configured to revolve about an imaging axis within the ring at a first radial distance, and to emit radiographic energy toward and across the imaging axis. A digital radiographic detector is positioned diametrically across the imaging axis from the source and is configured to revolve about the imaging axis at a second radial distance. The detector includes an array of photosensors disposed along a curved surface of the detector facing the imaging axis and the x-ray source.

In one embodiment, a mobile CBCT imaging system is constructed with a mobile base and a scanning ring electromechanically connected thereto. The scanning ring includes a source to emit radiographic energy and a detector to capture a radiographic image. The source and detector are positioned in relation to an imaging axis and the source is configured to revolve about the imaging axis and to emit radiographic energy toward the detector across the imaging axis. The detector includes an array of photosensors disposed along a curved surface facing the source.

In one embodiment, a mobile CBCT imaging system includes a wheeled mobile base, a movable column connected to the mobile base, and a movable imaging ring connected to the movable column. The imaging ring surrounds an imaging bore configured to receive an object to be radiographically imaged, such as the head and/or neck of a patient. The imaging ring includes an x-ray source and a detector to capture a radiographic image of the object. The source and detector may be fixed in diametrically opposed positions in relation to an imaging axis defined by the imaging ring. The source and detector may be configured to simultaneously revolve about the imaging axis while generating radiographic images of the object at a plurality of different imaging angles around the imaging axis. The detector includes an array of photosensors facing the imaging axis formed on a curved surface of the detector.

The summary descriptions above are not meant to describe individual separate embodiments whose elements are not interchangeable. In fact, many of the elements described as related to a particular embodiment can be used together with, and possibly interchanged with, elements of other described embodiments. In particular, elements disclosed herein may be combined with embodiments described in the patents identified above that are incorporated herein by reference. Many changes and modifications may be made within the scope of the present invention without departing from the spirit thereof, and the invention includes all such modifications. The drawings below are intended to be drawn neither to any precise scale with respect to relative size, angular relationship, relative position, or timing relationship, nor to any combinational relationship with respect to interchangeability, substitution, or representation of a required implementation.

This brief description of the invention is intended only to provide a brief overview of subject matter disclosed herein according to one or more illustrative embodiments, and does not serve as a guide to interpreting the claims or to define or limit the scope of the invention, which is defined only by the appended claims. This brief description is provided to introduce an illustrative selection of concepts in a simplified form that are further described below in the detailed description. This brief description is not intended to identify key features or essential features of the claimed subject matter, nor is it intended to be used as an aid in determining the scope of the claimed subject matter. The claimed subject matter is not limited to implementations that solve any or all disadvantages noted in the background.

BRIEF DESCRIPTION OF THE DRAWINGS

So that the manner in which the features of the invention can be understood, a detailed description of the invention may be had by reference to certain embodiments, some of which are illustrated in the accompanying drawings. It is to be noted, however, that the drawings illustrate only certain embodiments of this invention and are therefore not to be considered limiting of its scope, for the scope of the invention encompasses other equally effective embodiments. The drawings are not necessarily to scale, emphasis generally being placed upon illustrating the features of certain embodiments of the invention. In the drawings, like numerals are used to indicate like parts throughout the various views. Thus, for further understanding of the invention, reference can be made to the following detailed description, read in connection with the drawings in which:

FIG. 5 is a perspective view of the exemplary mobile imaging system of FIG. 1 illustrating a horizontal adjustment feature;

FIG. 6 is a perspective view of the exemplary mobile imaging system of FIG. 1 illustrating in close-up an engagement feature to provide stability during imaging;

FIGS. 7A-H illustrate exemplary detector and source embodiments of the imaging system of FIG. 1;

DETAILED DESCRIPTION OF THE INVENTION

Figure 1:
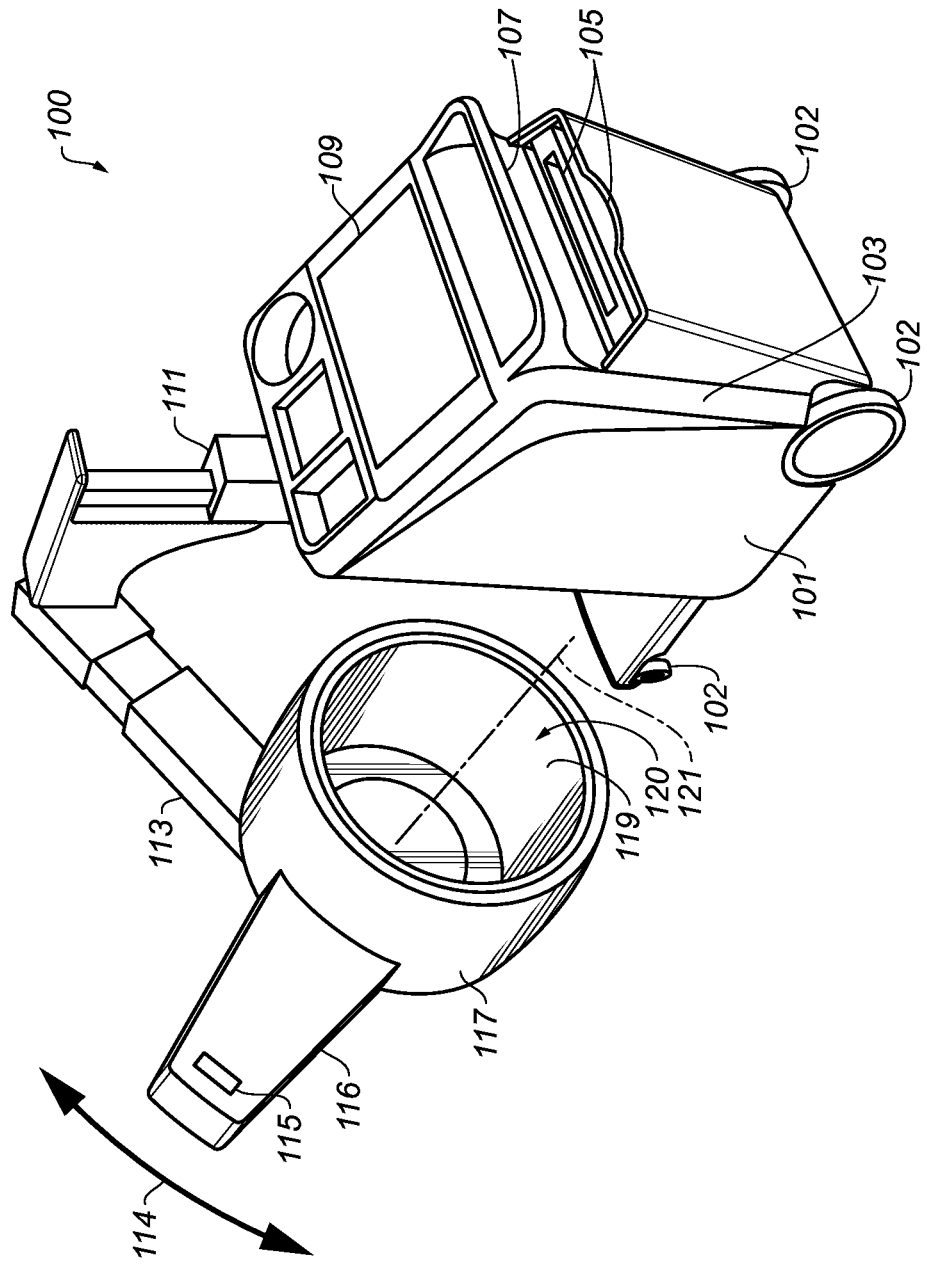
FIG. 1 is a perspective view of an exemplary mobile imaging system having an imaging ring.

FIG. 1 illustrates a mobile CBCT imaging system 100. The mobile imaging system 100 includes a mobile base 101 configured to travel across a floor or other surface, such as by manual manipulation using a handlebar 107, and rolled to a desired location. Wheels 102 attached to the mobile base 101 may be motor driven, such as by an electric motor powered by a rechargeable battery pack (not shown) housed in the mobile base 101; or the wheels 102 may be coupled to the mobile base 101 to allow the entire imaging system 100 to be pushed and rolled by one operator. The wheeled base 101 may include a processing system 103 for operating various features of the imaging system as described herein. A processing system including a processor and electronic memory may be housed in the mobile base 101 to provide image processing and image correction capabilities for digital images captured by the imaging system 100.

A display 109 is provided for viewing radiographic images transmitted to the mobile imaging system 100 or captured by the mobile imaging system 100. The display 109 may also be used to provide a touch screen GUI in electronic communication with the processing system 103 for an operator to input control instructions and other commands to operate the mobile CBCT imaging system, as described herein. Other input devices may also be provided proximate the top side of the mobile base 101 such as a keyboard and mouse, trackball, or other suitable input devices. A column 111 is rotatably attached to the mobile base 101 of the imaging system 100 and may be rotatable about a vertical axis 204 (FIG. 2), and may be height adjustable 201 (FIG. 2) and horizontally adjustable 501 (FIG. 5). An arm 113 is attached at one end to the column 111 and may be rotated about an attachment point 206 (FIG. 2) of the arm 113 to the column 111 as well as being extendable and retractable along its length 307 (FIG. 3). Portable, rechargeable, digital radiographic (DR) detectors of different sizes may be stored and/or charged in detector slots 105 provided at the mobile base 101.

An imaging ring, or scanning ring, 117 is attached to one end of the arm 113. As described herein, the imaging ring 117 includes one or more movable sources, one or more movable detectors, a rotating mechanism attached to the source(s) and detector(s), and a housing to enclose these components. The imaging ring includes one or more sources, such as source 115, to emit radiographic energy toward the one or more detectors 119 to capture radiographic images. The imaging ring 117 is configured to revolve at least one source 115 and at least one detector 119 about an imaging axis 121 in either a clockwise or counterclockwise direction as indicated by the double-headed arrow 114. The source 115 is positioned proximate one end of an extension 116 attached to the imaging ring 117 to increase a radial distance of the source 115 from the imaging axis 121. The imaging ring 117 may be configured to be translatable along the imaging axis 121 or transverse to the imaging axis 121 as described herein. In one embodiment, a detector 119 may be revolved simultaneously with a source 115 about the imaging axis 121 wherein the source 115 is positioned further from the imaging axis 121 than the detector 119 due to being affixed to the extension 116. In one embodiment, the detector 119 may revolve simultaneously with the source 115 while positioned diametrically opposite the source in relation to the imaging axis 121. The source 115 and detector 119 are positioned in relation to an imaging axis 121 so that the detector may capture one or more radiographic images of an object placed at or proximate to the imaging axis 121 within a bore surrounded by the imaging ring 117 and exposed to the radiographic energy emitted by the source 115. The interior of the imaging ring between the imaging axis 121 and an interior cylindrical surface of the imaging ring 117 may be referred to as the imaging bore. The imaging ring 117 includes an open end 120, visible in FIG. 1, configured to provide access for positioning an object proximate to the imaging axis 121 in the imaging bore to be radiographically imaged. The open end 120 faces in a direction toward a side of the imaging system 100 where an operator of the imaging system 100 may, at the same time, view the open end 120 of the imaging ring 117 while standing within reach of the display 109 to operate a touch screen GUI or other input devices described herein. The imaging ring 117 includes a closed end, visible in FIGS. 5-6, opposite the open end 120. Although not shown, the standard x-ray source 115 may include a collimator to appropriately shape an x-ray beam emitted by the source 115. The mobile base may also contain a generator electrically connected to the x-ray source 115 to provide power for firing the x-ray source 115.

As the source 115 and the detector 119 revolve about the imaging axis 121, the source 115 may be fired multiple times such that the detector 119 captures multiple images of an object positioned at or near the imaging axis 121. In one embodiment, the source 115 may be fired 60 times during a 360° revolution about the imaging axis 121 to generate 60 radiographic images captured in detector 119. In one embodiment, the source 115 may be fired 360 times during a 360° revolution about the imaging axis 121 to generate 360 radiographic images captured in detector 119. The source 115 may be fired any number of times during a revolution about the imaging axis 121. The source 115 and detector 119 may be revolved at less than 360° about an object positioned at imaging axis 121 to generate multiple radiographic images captured in detector 119.

Figure 2:
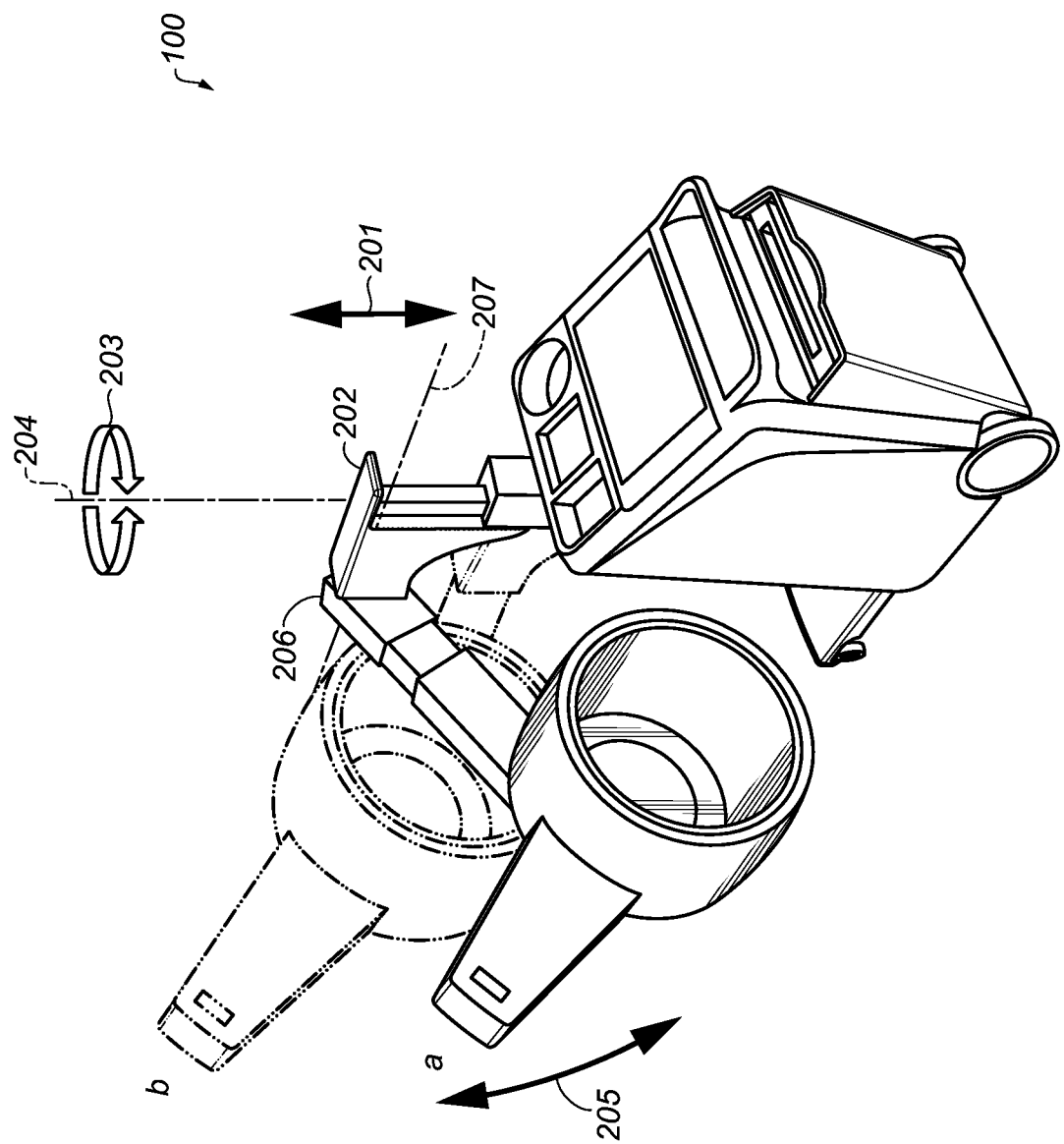
FIG. 2 is a perspective view of the exemplary mobile imaging system of FIG. 1 illustrating spatially adjustable positioning features.
Figure 3:
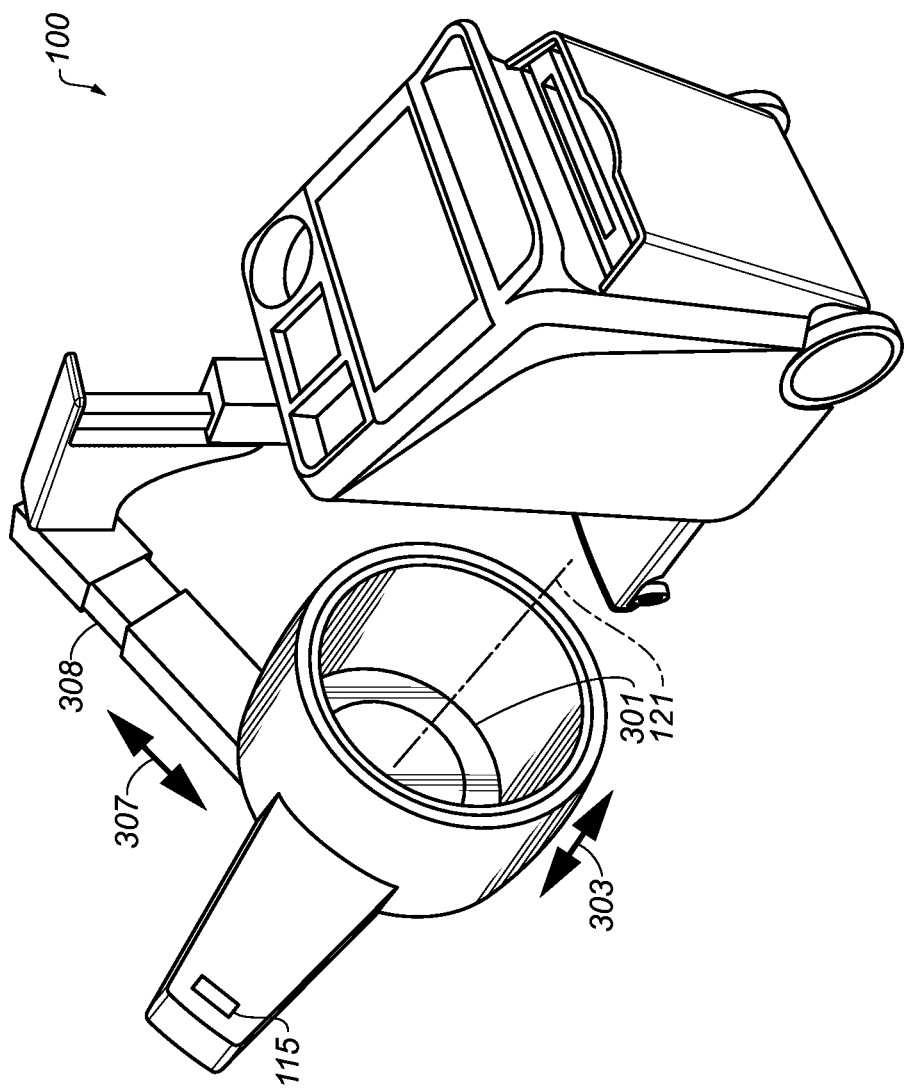
FIG. 3 is a perspective view of the exemplary mobile imaging system of FIG. 1 illustrating further spatially adjustable positioning features.

FIG. 2 shows some of the features of the imaging system 100 that allows spatially adjusting a position of the imaging ring 117. The column 111 includes a vertically slidable portion 202 allowing two-way movement of the column 111, as well as the arm 113 and imaging ring 117 attached thereto, along a vertical axis 204 as indicated by the double-headed arrow 201. The column 111 is also two-way rotatable relative to the mobile base 101 about the axis 204, as indicated by the arrows 203. The arm 113 is rotatably attached to the column 111 at attachment point 206 to allow two way rotational movement of the arm 113 and the imaging ring 117 about the axis 207 as indicated by the double-headed arrow 205. FIG. 2 illustrates two example rotational positions a, b, of the arm 113 and imaging ring 117.

FIG. 3 shows additional features of the imaging system 100 that allows spatially adjusting a position of the imaging ring 117. The arm 113 includes a telescoping portion 308 to allow the arm 113 to be extended or retracted along its length as indicated by the double-headed arrow 307. The imaging ring 117 itself may be attached to the arm 113 by a telescoping carriage (not shown) to allow the imaging ring 117 to be extended away from or closer to the arm 113 along imaging axis 121 as indicated by the double-headed arrow 303. The interior surface of the imaging ring 117 may have the shape of a cylinder with a width parallel to the imaging axis 121. In one embodiment, the imaging bore may be illuminated by one or more light sources affixed to the imaging ring 117. In one embodiment, the imaging bore may include a circular light source 301 proximate the closed end of the imaging bore.

Figure 4:
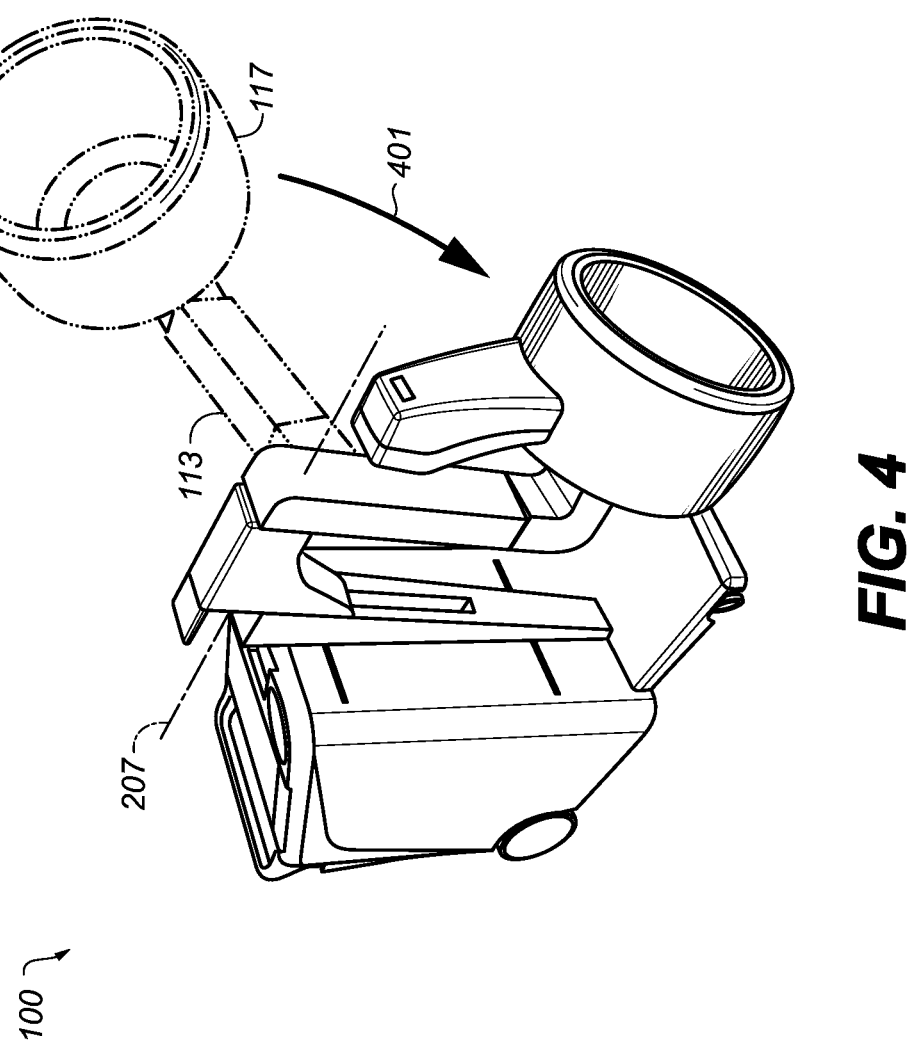
FIG. 4 is a perspective view of the exemplary mobile imaging system of FIG. 1 illustrating a rotatable arm feature.

As shown in FIG. 4, the imaging ring 117 and arm 113 of imaging system 100 may be rotated about axis 207 in the direction indicated by the arrow 401 to a lowered, or stowed, position suitable for transporting the imaging system 100 such as by rolling the imaging system 100 to an intended location at a medical facility. The stowed position of the imaging ring 117 and arm 113 clears a line of sight for an operator to see straight ahead while steering and/or pushing the imaging system 100 to an intended location. As shown in FIG. 5, the imaging system 100 may be configured such that the column 111 is movably attached to the mobile base 101 through slots 502 in the mobile base to allow bilateral movement of the column 111, together with the arm 113 and the imaging ring 119, in the directions indicated by the double-headed arrow 501. In one embodiment, the imaging ring 117 may be configured to allow spatial adjustment thereof to be performed manually. In one embodiment, spatial movement of the column and/or the arm may be motorized and controlled by input control devices provided at the mobile base 101, such as buttons or toggle switches, or via a touch screen GUI on display 109.

As shown in FIG. 6, the imaging ring 117 includes a "foot" 601 that may be moved vertically, as indicated by the double-headed arrow 602, to match a height of a patient bed. The foot 601 may be used to mechanically engage a mating feature located on a patient bed frame. Once mechanically engaged, the mating feature on the patient's bed and the foot 601 may serve to mechanically spatially stabilize the imaging ring 117 during an imaging procedure to minimize shaking and/or vibrations in the imaging ring 117.

Figure 7H:
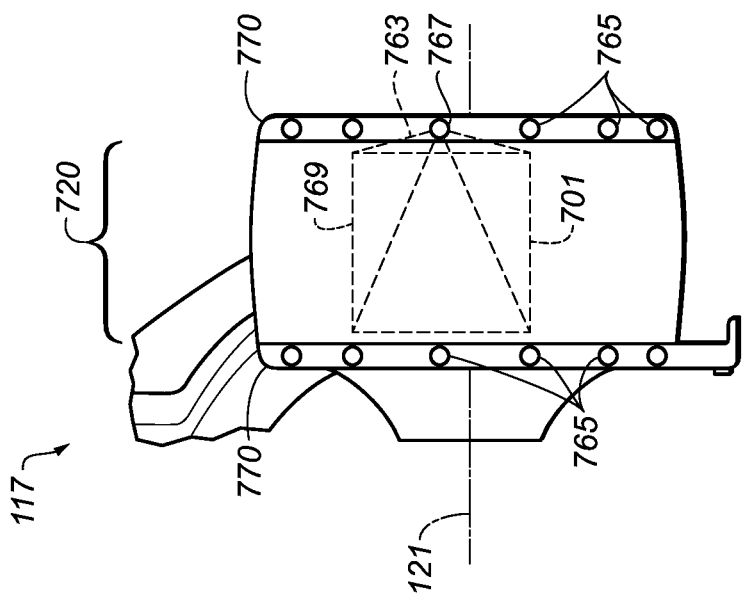

FIGS. 7A-H show front views, and a side view (FIG. 7H), of various embodiments of x-ray sources and DR detectors that may be used in the imaging ring 117. The one or more detector embodiments described herein each include a two-dimensional array of photosensors disposed along a surface of the detector, which surface faces the imaging axis, and is configured to receive x-rays from the one or more x-ray sources disposed in the imaging ring 117. The array of photosensors may be disposed across a curved detector surface or a planar detector surface. The curved surface of the detector may be formed in the shape of a portion of a cylinder or it may be curved in two-dimensions such as a parabolic surface. The curved surface of the detector may embody a radius of curvature equivalent to a radius of curvature of the imaging ring 117 or it may be different. For example, a planar detector may fit within the imaging ring 117 as described herein. Thus, the one or more detectors in the imaging ring may include one or more planar detectors, or a combination of planar and curved detectors. As shown in FIG. 7A, an x-ray source 115 is positioned within and proximate to one end of the imaging ring extension 116 and emits an x-ray beam 703 that radiates toward the imaging axis 121 to a curved DR detector 701 disposed at a position diametrically opposed to the x-ray source 115. In one embodiment as shown in FIG. 7A, the curved detector 701 may extend around a circumference of the imaging ring 117 for about 90° and have a width about the same as or less than a width 720 (FIG. 7H) of the imaging ring 117. In one embodiment as shown in FIG. 7B, the curved detector 711 may extend around a circumference of the imaging ring 117 for about 180° and have a width about the same as or less than a width 720 of the imaging ring 117. In one embodiment, the detectors 701, 711, may include a curvature, or contour, shaped in the form of a portion of a cylinder. The curvature of the detector 701, 711, may exactly or approximately match a curvature of the imaging ring 117. The detector 701, 711, may extend around a circumference of the imaging ring 117 for less than 90° or for more than 180°, such as a 360° circular (full cylinder) detector having a width about the same as or less than a width 720 of the imaging ring 117. In the embodiments of FIGS. 7A-B only one curved detector is positioned in the imaging ring 117 for image capture.

In one embodiment as shown in FIG. 7C, the imaging ring 117 may include multiple detectors 721-723. The one or more detectors 721-723 in the imaging ring 117 may include multiple curved detectors of different circumferential lengths (measured by angle subtended) and different widths. The multiple curved detectors 721-723 may be arranged such that their adjacent edges abut 725, or have a gap 727 therebetween, or overlap (FIG. 7F), or any combination thereof. In one embodiment as shown in FIG. 7D, the imaging ring 117 may include multiple planar shaped detectors 731 arranged adjacent to each other having a gap therebetween. However, the multiple planar shaped detectors 731 may be arranged in other orientations as described herein. In one embodiment as shown in FIG. 7E, the imaging ring 117 may include multiple planar shaped detectors 742-743 arranged adjacent to a middle curved detector 741, wherein the planar detector 742 abuts middle curved detector 741 and the planar detector 743 is spaced apart from the middle curved detector 741. In one embodiment as shown in FIG. 7F, the imaging ring 117 may include multiple curved detectors 751-753 arranged such that an edge of detectors 751, 753, each overlap an opposite edge of the middle curved detector 752. Any embodiment of the single or multiple detector arrangements described herein may be configured to remain stationary during an image capture procedure while a position of an x-ray source, when fired, may vary around the imaging axis 121. Embodiments of the single or multiple detector arrangements may also be configured to rotate simultaneously with a source about the imaging axis during an image capture procedure. As illustrated herein, the imaging ring 117 may be configured such that a source 115 of the imaging system is positioned at a distance from the imaging axis 121 greater than the distance from the detector 109 to the imaging axis 121.

Figure 7G:
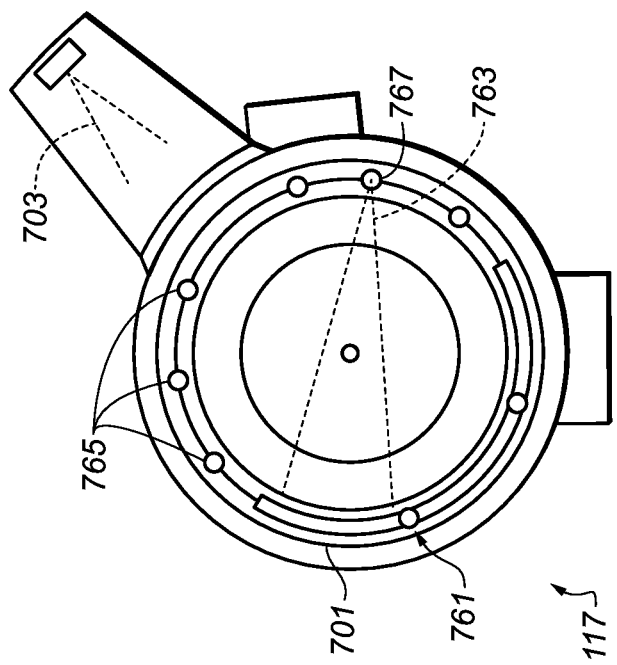

In one embodiment, shown in FIG. 7G, a plurality of carbon nanotube (CNT) x-ray sources 765 may be used in place of, or together with, the standard x-ray source 115. The CNT sources 765 may be fixed at various positions in association with the imaging ring 117. The CNT sources 765 may be positioned at regular or irregular circumferential intervals about the imaging ring 117. The CNT sources 765 may include a collimator (not shown) so that their emitted x-ray beams target one or more selected detectors or a selected detector exposure area. In one embodiment, such as shown in FIG. 7G, using one or more detectors 701 extending about a circumferential curvature of the imaging ring, or even 360° around the circumference of the imaging ring 117, the plurality of CNT sources 765 may each be positioned approximately at a middle of the width 720 of the imaging ring 117, for example, in a gap 761 between spaced apart adjacent detectors. In one embodiment, a plurality of CNT sources may be positioned at one or both annular edges of the imaging ring, at the open end of the imaging ring 117 or at the closed end, or both, such as shown in FIG. 7H. The various CNT sources 765, as well as the source 115, may be aimed toward an imaging surface of one or more detectors such as shown in FIGS. 7G-H. In one example illustrated in FIGS. 7G-H, a selected one of the CNT sources 767 is energized, or fired, to emit an x-ray beam 763 toward a detector 701. A collimator (not shown) may be used to shape the emitted x-ray beam 763 from the energized source 767 that targets an imaging area 769 of one or more detectors 701 for exposure. As shown in FIG. 7H, an imaging area 769 of the detector 701 includes a width less than a width 720 of the imaging ring 117. In one embodiment, the CNT sources 765 may be selectively energized in a predetermined programmed sequence to capture a plurality of radiographic images at various angles about the imaging ring 117. In such an embodiment of sequentially activated CNT sources the detector 701 may be configured to revolve about the imaging axis 121 until it reaches a position to adequately capture a radiographic image generated by an activated stationary CNT source. In such an embodiment of sequentially activated CNT sources a plurality of stationary detectors may each capture a radiographic image generated by an activated stationary CNT source. In one embodiment, one or more of the CNT sources 765 positioned at the annular edges of the imaging ring 117 (FIG. 7H) may be stationary CNT sources attached to a portion 770 of the imaging ring 117 that does not revolve. In one embodiment, one or more of the CNT sources 765 may be attached to a portion of the imaging ring 117 that revolves. In one embodiment, one or more stationary detectors, such as detector 701, may be attached to a portion of the imaging ring that does not revolve.

Figure 8:
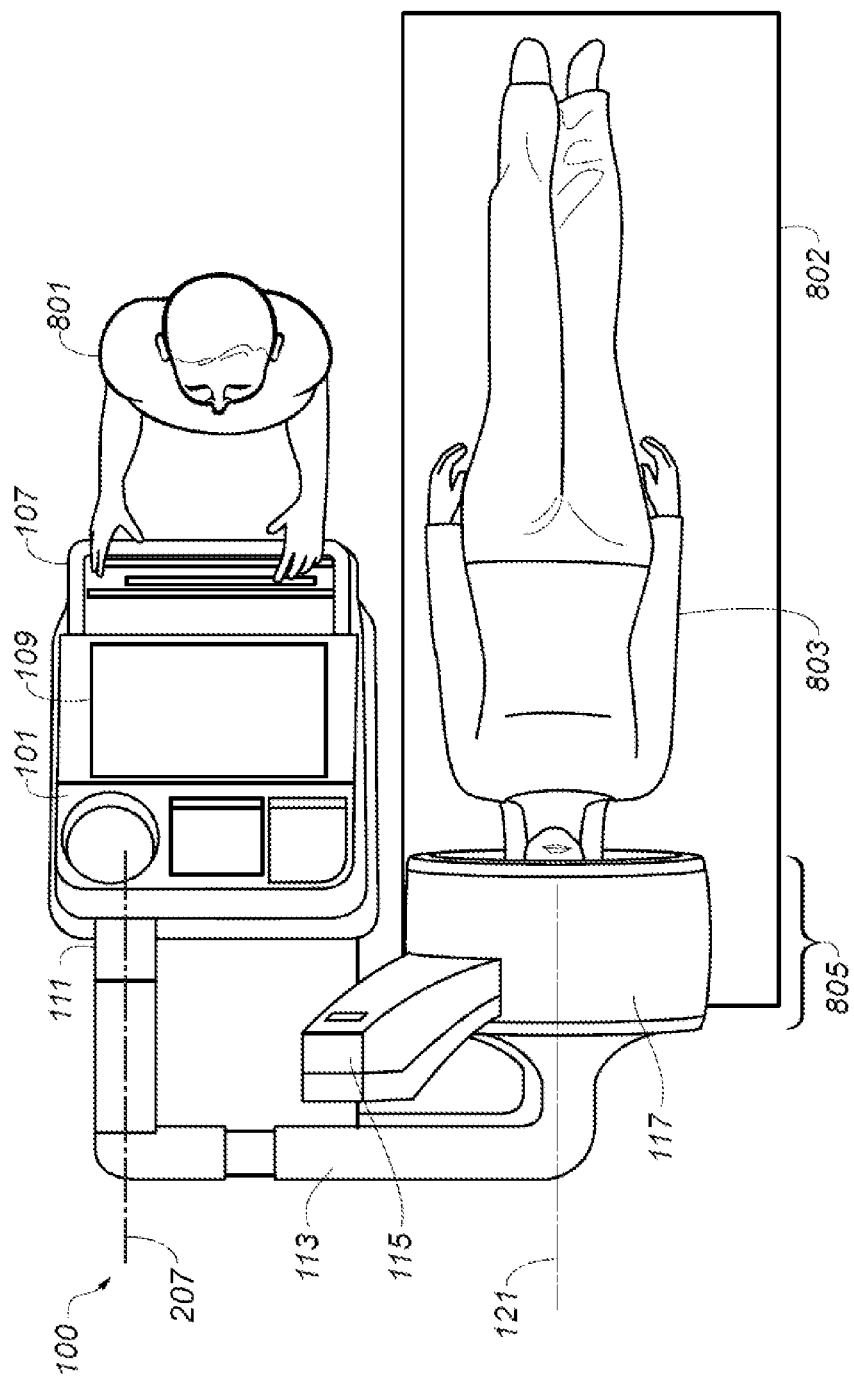
FIG. 8 illustrates an exemplary patient scanning position of the imaging system of FIG. 1.

FIG. 8 illustrates an operator 801 using the imaging system 100 to obtain radiographic images of the head of a patient 803 that is partially positioned within the bore of the imaging ring 117. The width of the imaging bore 805 is sufficient to image the head of the patient 803 from at least about a top of the head of the patient 803 to approximately near the collar bone of the patient 803. As shown in FIG. 8, an operator 801 can view a position of the head of the patient 803 in the imaging bore of the imaging ring 117 while at the same time accessing the handlebar 107 of the imaging system 100 or other controls at the mobile base 101 of the imaging system 100. In particular, the operator 801 may position the mobile imaging system 100 near a bed 802 having a patient 803 to be imaged lying thereon. The operator 801 may manipulate the imaging ring 117 as described herein to position it such that the patient's head is at least partially located at or proximate to the imaging axis within a width 805 of the imaging ring 117. As shown in FIG. 8, the imaging system 100 is configured so that the open end of the imaging ring 117 faces (to the right in FIG. 8) in a direction generally opposite to a direction that an operator 801 is facing (to the left in FIG. 8) when standing in a position to operate the controls (e.g. handle bar 107, GUI interface on display 109) of the imaging system 100. A position of the operator 801 wherein the operator 801 may facilitate placement of the imaging ring 117 around the head of a patient 803 ensures convenient usage of the imaging system 100, which includes keeping the open end of the imaging ring 117 in the operator's line of sight while the operator 801 is operating controls near the top of the mobile base 101 of the imaging system 100, and allowing the operator 801 to reach the controls of the imaging system 100 while remaining close to, i.e., adjacent and within arm's reach of, the patient 803.

An imaging procedure, such as a scan, may be performed by the operator 801 activating controls at the mobile base 101 of the imaging system 100, such as to power up an x-ray generator and to activate an x-ray source, such as x-ray source 115. One or more detectors may also be activated, and then one or both the source 115 and the one or more detectors (not shown in FIG. 8) may be revolved about the imaging axis to capture a plurality of ra' diographic images of the head and/or neck of the patient 803 in the one or more detectors. In one embodiment using fixed CNT sources, as described herein, and a fixed or rotating detector(s), the CNT sources may be fired sequentially to obtain a plurality of radiographic images equivalent to those obtained using a rotating x-ray source, or a rotating x-ray source and rotating detector. A plurality of images captured by such a scanning procedure may be reconstructed using known programmed algorithms to generate 3D volume images of the patient's head and/or neck.

Figure 9:
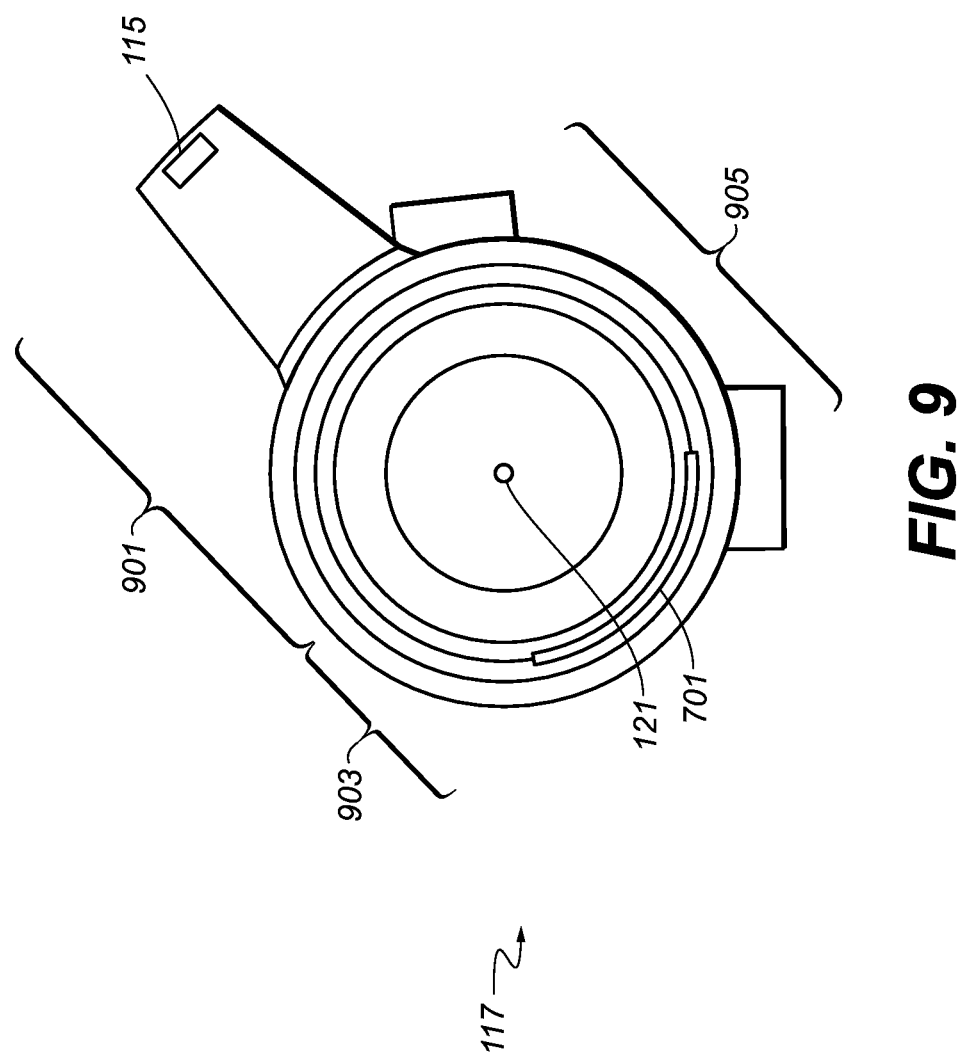
FIG. 9 illustrates exemplary dimensions of components of the imaging ring of the imaging system of FIG. 1.

FIG. 9 illustrates several dimensions of the imaging ring 117, showing that a distance 901 between the x-ray source 115 and the imaging axis 121 is greater than a distance 903 between the detector 701 and the imaging axis 121. As the source 115 and the detector 701 rotate about the imaging axis 121 during an imaging procedure to capture radiographic images of an object placed at or near the imaging axis 121, the distances 901 and 903 are maintained throughout the entire imaging procedure. A diameter 905 of the imaging ring 117 may refer to a diameter of the orbit of the detector 701 around imaging axis 121.

Figure 10C:
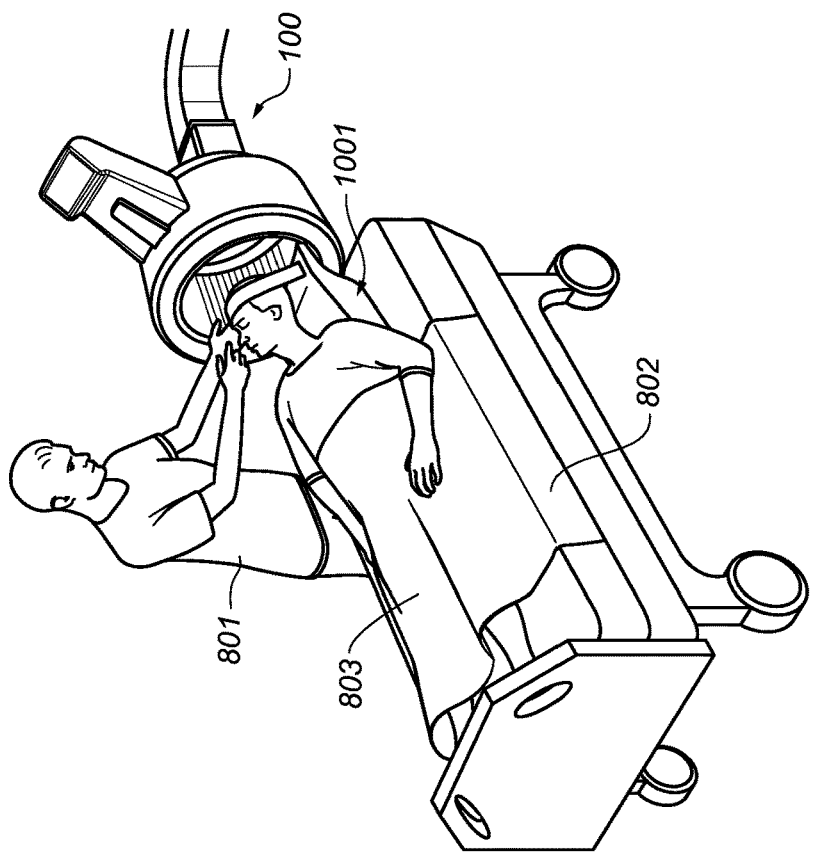
FIGS. 10A-C illustrate an exemplary head support for use with the mobile imaging system of FIG. 1.
Figure 10A:
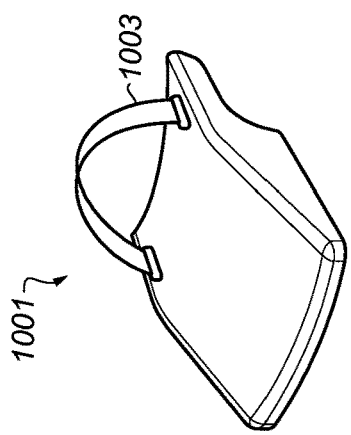
Figure 10B:
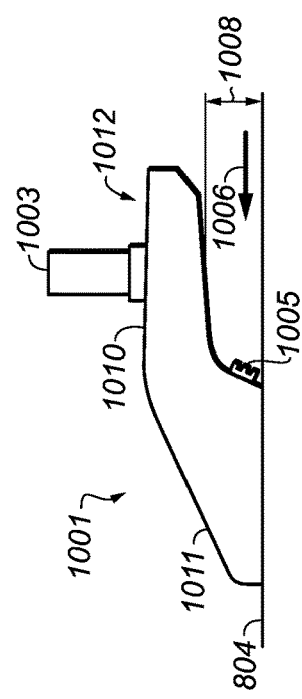

FIGS. 10A-C illustrate a head support 1001 that may be advantageously used together with the mobile imaging system 100 described herein. The head support 1001 is configured to support the head of a patient 803 above a surface 804 of a bed 802 whereupon the patient 803 lies. One surface 1010 of the head support 1001 is designed to support the head of the patient 803 while another surface 1011 of the head support 1001, is designed to support the neck or upper back of the patient 803. The surface 1011 is shaped to form an angle to the surface 1010. The head support 1001 may be placed on a top surface 804 of the bed under the patient's upper back and/or neck as shown in FIG. 10C. A head support strap 1003 connected to the head support 1001 may be provided to wrap around a portion of the patient's head to securely fit the patient's head on the head support 1001. The head support 1001 may be made entirely or partly from a cushioned or padded material, or other soft material such as a rubber foam material, having a suitable rigidity or other rigid structural components within the head support to support the patient's head. The head support 1001 provides a clearance 1008 between a top surface 804 of the bed 802 and an overhanging portion 1012 of the head support 1001 to allow part of the imaging ring 117 to be positioned in the direction of arrow 1006 under the patient's head and/or neck, as it rests on the head support 1001, and under the overhanging portion 1012 of the head support 1001, thereby allowing the imaging ring 117 to surround the patients head and/or neck (FIG. 10C) for proper CBCT imaging exposure and image capture. The head support 1001 may include an attachment feature, or locking mechanism, 1005 configured to securely engage a mating feature (not shown) on an annular edge of the imaging ring 117 at the open end of the imaging ring 117 so that the imaging ring 117 may be firmly secured to the head support 1001 during an imaging procedure.

Figure 11:
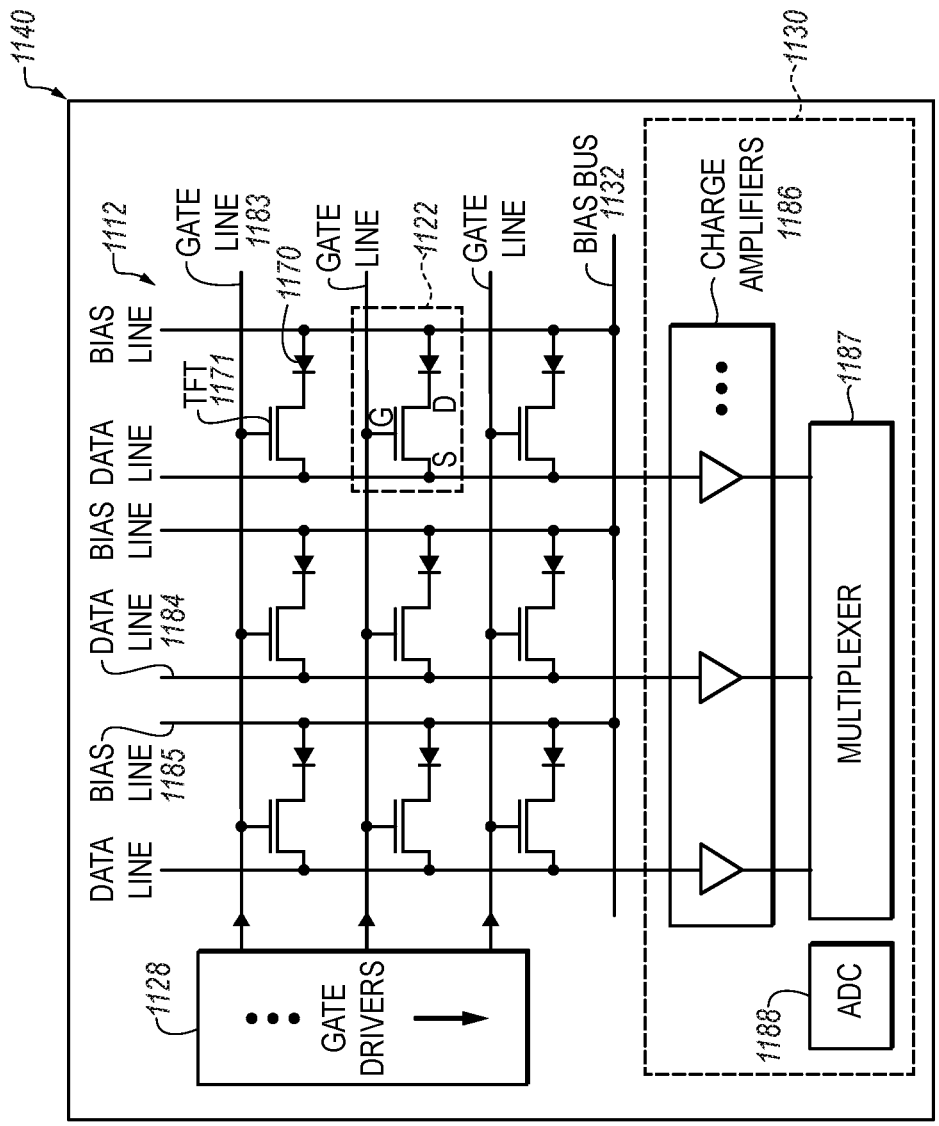
FIG. 11 is a schematic diagram of a two dimensional array of photosensors.

FIG. 11 is a schematic diagram 1140 of a portion of a two-dimensional array of photosensors 1112 usable with a curved DR detector, such as DR detectors 701, 711 described herein. The array of photosensors 1112, whose operation may be consistent with the array of photosensors described above, may include a number of hydrogenated amorphous silicon (a-Si:H) n-i-p photodiodes 1170 and thin film transistors (TFTs) 1171 formed as field effect transistors (FETs) each having gate (G), source (S), and drain (D) terminals. In embodiments of a DR detector 701 disclosed herein, such as a multilayer DR detector (1300 of FIG. 13), the two-dimensional array of photosensor cells 1112 may be formed in a device layer that abuts adjacent layers of the DR detector structure, which adjacent layers may include a flexible polyimide layer or a layer including carbon fiber. A plurality of gate driver circuits 1128 may be electrically connected to a plurality of gate lines 1183 which control a voltage applied to the gates of TFTs 1171, a plurality of readout circuits 1130 may be electrically connected to data lines 1184, and a plurality of bias lines 1185 may be electrically connected to a bias line bus or a variable bias reference voltage line 1132 which controls a voltage applied to the photodiodes 1170. Charge amplifiers 1186 may be electrically connected to the data lines 1184 to receive signals therefrom. Outputs from the charge amplifiers 1186 may be electrically connected to a multiplexer 1187, such as an analog multiplexer, then to an analog-to-digital converter (ADC) 1188, or they may be directly connected to the ADC, to stream out the digital radiographic image data at desired rates. In one embodiment, the schematic diagram of FIG. 11 may represent a portion of a DR detector 701 such as an a-Si:H based indirect curved panel or flexible panel imager.

Incident x-rays, or x-ray photons, are converted to optical photons, or light rays, by a scintillator, which light rays are subsequently converted to charges upon impacting the a-Si:H n-i-p photodiodes 1170. In one embodiment, an exemplary detector cell 1122, which may be equivalently referred to herein as a photosensor, may include a photodiode 1170 having its anode electrically connected to a bias line 1185 and its cathode electrically connected to the drain (D) of TFT 1171. The bias reference voltage line 1132 can control a bias voltage of the photodiodes 1170 at each of the detector cells 1122. The charge capacity of each of the photodiodes 1170 is a function of its bias voltage and its capacitance. In general, a reverse bias voltage, e.g. a negative voltage, may be applied to the bias lines 1185 to create an electric field (and hence a depletion region) across the pn junction of each of the photodiodes 1170 to enhance its collection efficiency for the charges generated by incident light rays. The image signal represented by the array of photosensor cells 1112 may be integrated by the photodiodes while their associated TFTs 1171 are held in a non-conducting (off) state, for example, by maintaining the gate lines 1183 at a negative voltage via the gate driver circuits 1128. The photosensor cell array 1112 may be read out by sequentially switching rows of the TFTs 1171 to a conducting (on) state by means of the gate driver circuits 1128. When a row of the photosensors 1122 is switched to a conducting state, for example by applying a positive voltage to the corresponding gate line 1183, collected charge from the photodiode in those photosensors may be transferred along data lines 1184 and integrated by the external charge amplifier circuits 1186. The row may then be switched back to a non-conducting state, and the process is repeated for each row until the entire array of photosensors 1112 has been read out. The integrated signal outputs are transferred from the external charge amplifiers 1186 to an analog-to-digital converter (ADC) 1188 using a parallel-to-serial converter, such as multiplexer 1187, which together comprise read-out circuit 1130.

This digital image information may be subsequently processed by the processing system in mobile base 101 to yield a radiographic digital image which may then be digitally stored and immediately displayed on display 109, or it may be displayed at a later time by accessing a digital electronic memory of the processing system containing the stored image. The curved DR detector 701 having an imaging array as described with reference to FIG. 11 may be capable of both single-shot (e.g., static, radiographic) and continuous rapid image acquisition.

Figure 12:
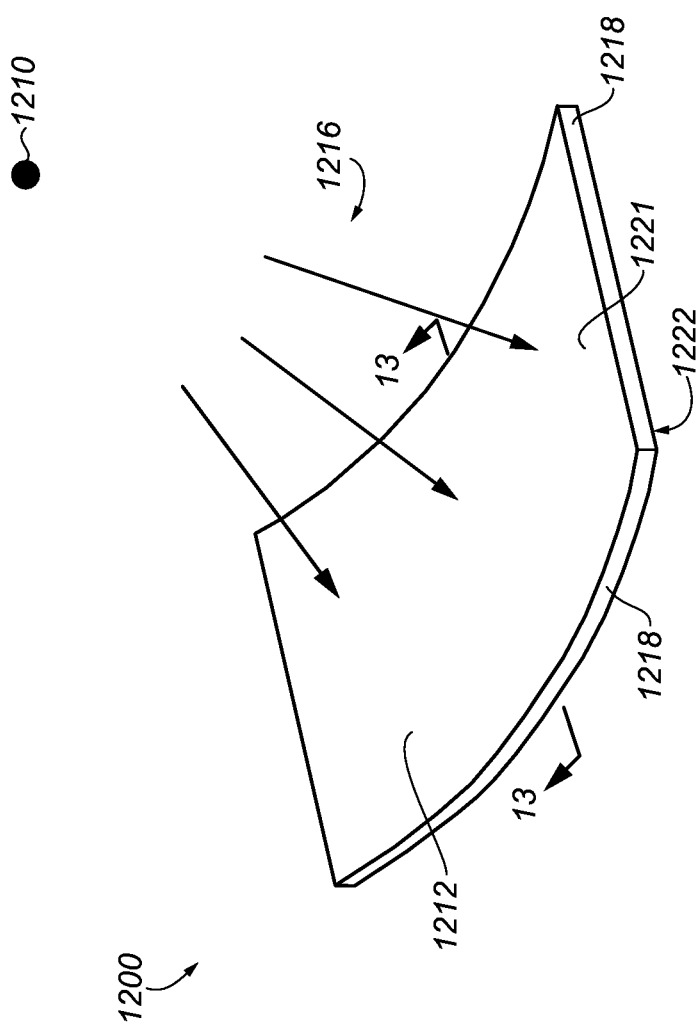
FIG. 12 shows a perspective view of an exemplary curved DR detector.

FIG. 12 shows a perspective view of an exemplary curved portable wireless DR detector 1200 according to an embodiment of the DR detectors 701 disclosed herein. The DR detector 1200 may include a flexible substrate to allow the DR detector to capture radiographic images in a curved orientation. The flexible substrate may be fabricated in a permanent curved orientation, or it may remain flexible throughout its life to provide an adjustable curvature in two or three dimensions, as desired. The DR detector 1200 may include a similarly flexible housing portion 1214 that surrounds a multilayer structure comprising a flexible array of photosensors 1122 of the DR detector 1200. The housing portion 1214 of the DR detector 1200 may include a continuous, flexible, radiopaque material, surrounding an interior volume of the DR detector 1200. The housing portion 1214 may include four flexible edges 1218, extending between the top side 1221 and the bottom side 1222, and arranged substantially orthogonally in relation to the top and bottom sides 1221, 1222. The bottom side 1222 may be continuous with the four edges and disposed opposite the top side 1221 of the DR detector 1200. The top side 1221 comprises a top cover 1212 attached to the housing portion 1214 which, together with the housing portion 1214, substantially encloses the multilayer structure in the interior volume of the DR detector 1200. The top cover 1212 may be attached to the housing 1214 to form a seal therebetween, and be made of a radiolucent material that passes x-rays 1216 without significant attenuation thereof, such as a carbon fiber plastic, polymeric, or other plastic based material. The x-rays 1216 may be emitted at a focal point 1210 of an x-ray source 115. The top side 1221 of the curved DR detector 1200 may be oriented such that the emitted x-rays 1216 impact each of the photosensors at an angle that is closer to a perpendicular (90°) angle for most of the photosensors than using a planar panel detector. In particular, such a curved detector 1200 may be advantageously used in a CBCT imaging system wherein a radial distance between an imaging axis 121 and the DR detector 701 is small.

Figure 13:
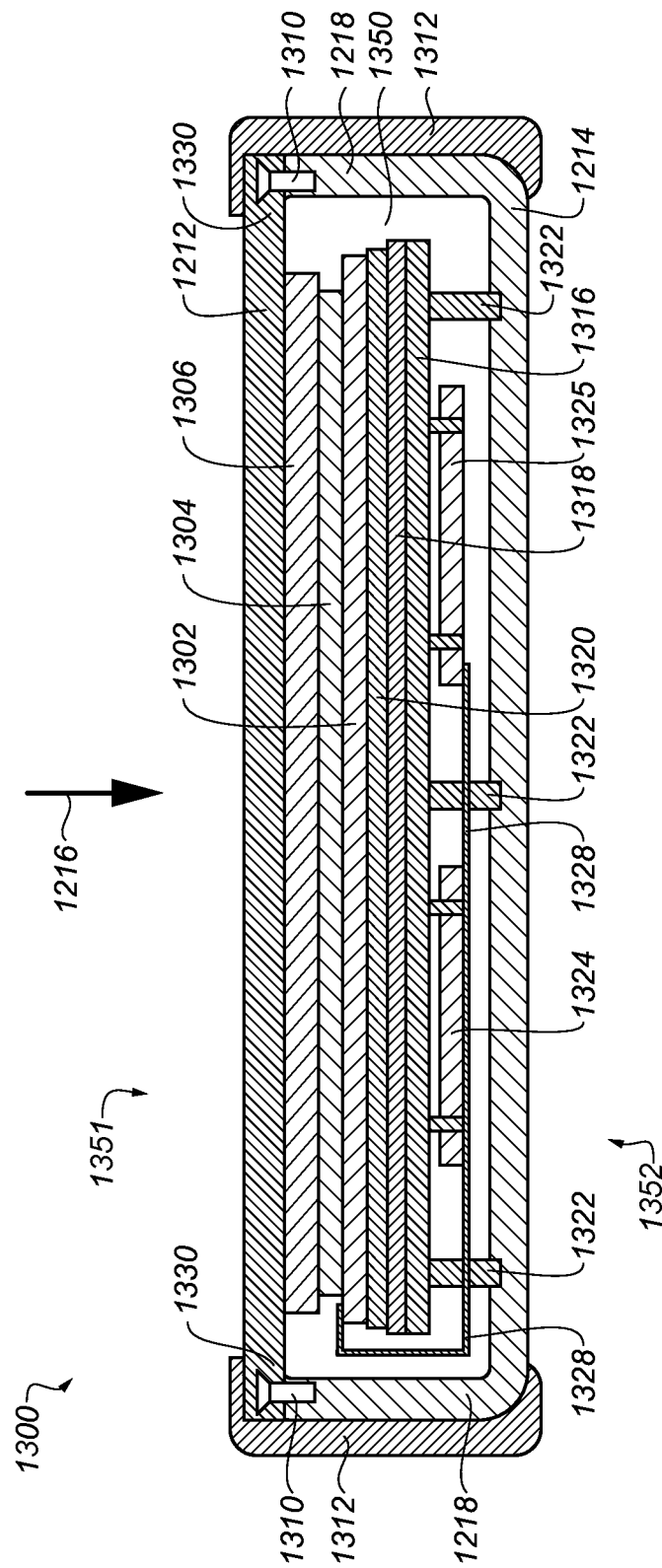
FIG. 13 shows a cross-section view of the curved DR detector of FIG. 12.

With reference to FIG. 13, there is illustrated in schematic form an exemplary cross-section view along section 13-13 of the exemplary embodiment of the DR detector 1200 (FIG. 12). For spatial reference purposes, one major surface of the DR detector 1300 may be referred to as the top side 1351 and a second major surface may be referred to as the bottom side 1352, as used herein. The multilayer structure may be disposed within the interior volume 1350 enclosed by the housing 1214 and top cover 1212 and may include a flexible curved scintillator layer 1304 over a curved two-dimensional array of photosensors 1112 shown schematically as the device layer 1302. The scintillator layer 1304 may be directly under (e.g., directly connected to) the substantially planar top cover 1212, and the imaging array 1302 may be directly under the scintillator 1304. Alternatively, a flexible layer 1306 may be positioned between the scintillator layer 1304 and the top cover 1212 as part of the multilayer structure to allow adjustable curvature of the multilayer structure and/or to provide shock absorption. The flexible layer 1306 may be selected to provide an amount of flexible support for both the top cover 1212 and the scintillator 1304, and may comprise a foam rubber type of material. The layers just described comprising the multilayer structure each may generally be formed in a curved rectangular shape and defined by edges arranged orthogonally and disposed in parallel with an interior side of the edges 1218 of the housing 1214, as described in reference to FIG. 12.

A flexible substrate layer 1320 may be disposed under the imaging array 1302, such as a flexible polyimide or carbon fiber upon which the array of photosensors 1302 may be formed to allow adjustable curvature of the array. Under the substrate layer 1320 a radiopaque shield layer 1318 may be used as an x-ray blocking layer to help prevent scattering of x-rays passing through the substrate layer 1320 as well as to block x-rays reflected from other surfaces in the interior volume 1350. Readout electronics, including the read out circuits described in relation to FIG. 11 may be formed adjacent the imaging array 1302 or, as shown, may be disposed below frame support member 1316 in the form of small integrated circuits (ICs) electrically connected to printed circuit substrates 1324, 1325. The imaging array 1302 may be electrically connected to the readout electronics 1324 (ICs) over a flexible connector 1328 which may comprise a plurality of flexible, sealed conductors known as chip-on-film (COF) connectors.

X-ray flux may pass through the radiolucent top panel cover 1212, in the direction represented by an exemplary x-ray beam 1216, and impinge upon scintillator 1304 where stimulation by the high-energy x-rays 1216, or photons, causes the scintillator 1304 to emit lower energy photons as visible light rays which are then received in the photosensors of imaging array 1302. The frame support member 1316 may connect the multilayer structure to the housing 1214 and may further operate as a shock absorber between the frame support beams 1322 and the housing 1214. Fasteners 1310 may be used to attach the top cover 1212 to the housing 1214 and create a seal therebetween in the region 1330 where they come into contact. In one embodiment, an external bumper 1312 may be attached along the edges 1218 of the DR detector 1300 to provide additional shock-absorption.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A mobile CBCT imaging system comprising:
a wheeled mobile base;
a movable column connected to the mobile base, the movable column configured to move vertically along a vertical axis;
a movable imaging ring connected to an extendable arm, the extendable arm connected to the movable column and configured to move vertically together with the movable column, the extendable arm further configured to rotate about an arm rotation axis that extends through the vertical column, the extendable arm further configured to move the imaging ring closer to and further from the arm rotation axis, the imaging ring surrounding an imaging bore configured to receive an object to be radiographically imaged, the imaging ring comprising:
a source to emit radiographic energy; and
a detector to capture a radiographic image of the object;
a head support configured to lie on a surface of a bed and to elevate and support a head of a patient lying on the surface of the bed, the head of the patient being supported above the surface of the bed with a clearance therebetween such that a portion of the imaging ring is permitted to travel into the clearance between the head support and the surface of the bed, thereby allowing the imaging ring to surround the head of the patient,
wherein the source and detector are fixed in diametrically opposed positions in relation to an imaging axis defined by the imaging ring, and wherein the source and detector are configured to simultaneously revolve about the imaging axis while generating radiographic images of the object at a plurality of different imaging angles.

2. A mobile CBCT imaging system comprising:
a wheeled mobile base;
a movable vertical column connected to the mobile base, the vertical column configured to move vertically along a vertical axis relative to the mobile base;
an extendable arm connected to the movable vertical column and configured to rotate relative to the vertical column about a extendable arm rotation axis that intersects the vertical column, the extendable arm further configured to extend further from the extendable arm rotation axis along an arm extension axis and retract closer to the extendable arm rotation axis along the arm extension axis; and
an imaging ring connected to the extendable arm such that the imaging ring revolves about the extendable arm rotation axis when the extendable arm rotates about the extendable arm rotation axis and such that the imaging ring moves further from and closer to the extendable arm rotation axis as the extendable arm extends and retracts, the imaging ring comprising:
a source to emit radiographic energy, the source configured to revolve about an imaging axis; and
a detector configured to revolve about the imaging axis simultaneously with the source, the detector comprising an array of photosensors to capture a radiographic image of a subject positioned proximal to the imaging axis between the source and the detector,
wherein the imaging axis is substantially parallel to the extendable arm rotation axis.

3. The system of claim 2, wherein the imaging ring is configured to be movable parallel to the imaging axis further from and closer to the extendable arm.

4. The system of claim 2, further comprising:
a bed; and
a head support configured to lie on a surface of the bed and to elevate and support a head of a patient lying on the surface of the bed, the head of the patient being supported above the surface of the bed such that a portion of the imaging ring has sufficient clearance to travel between the head support and the surface of the bed, thereby allowing the imaging ring to surround the head of the patient.

5. The system of claim 2, wherein the head support comprises an engagement feature for rigidly securing the head support to the imaging ring during an imaging procedure.

6. The system of claim 2, wherein the imaging ring comprises a closed end and an open end opposite the closed end, the open end for receiving a head of the subject to be imaged, the closed end is attached to the extendable arm, and wherein the imaging axis intersects the closed end.

7. The system of claim 2, wherein the imaging axis remains substantially parallel to the extendable arm rotation axis while the imaging ring revolves about the horizontal axis.

8. The system of claim 2, wherein the imaging ring comprises a plurality of individual detectors facing the imaging axis.

9. The system of claim 8, wherein the plurality of individual detectors are arranged such that their adjacent edges are spaced apart, overlap or abut.

10. The system of claim 2, wherein a radial distance between the source and the imaging axis is greater than a radial distance between the detector and the imaging axis during an entire revolution of the source and detector about the imaging axis.

11. The system of claim 2, wherein the imaging ring comprises a plurality of stationary carbon nanotube x-ray sources.

12. The system of claim 11, wherein the plurality of stationary carbon nanotube x-ray sources are distributed along a periphery of the imaging ring.

13. The system of claim 12, wherein the plurality of stationary carbon nanotube x-ray sources are disposed along one or two annular edges of the imaging ring.

14. The system of claim 12, wherein the plurality of stationary carbon nanotube x-ray sources are each collimated to emit an x-ray beam toward an imaging area of the detector.

15. The system of claim 2, wherein a curvature of the curved detector is equivalent to a curvature of the imaging ring.

16. The system of claim 15, wherein the curved detector comprises a shape in the form of a portion of a cylinder.

17. The system of claim 15, wherein the curvature of the imaging ring comprises a cylindrical curvature.

18. A mobile CBCT imaging system comprising:
a bed;
a head support configured to lie on a surface of the bed, to elevate and support a head of a patient lying on the surface of the bed, and to provide clearance between the head support and the surface of the bed;
a wheeled mobile base;
a movable arm connected to the mobile base;
an imaging ring connected to the movable arm, the imaging ring comprising:
a source to emit radiographic energy, the source configured to revolve about an imaging axis; and
a detector configured to revolve about the imaging axis simultaneously with the source to capture a radiographic image of the head of the patient positioned proximal to the imaging axis between the source and the curved detector; and
wherein the head of the patient is supported above the surface of the bed by the head support such that the clearance between the head support and the surface of the bed is sufficient for a portion of the imaging ring to travel between the head support and the surface of the bed to surround the head of the patient.

19. The system of claim 18, wherein the head support comprises an engagement feature for rigidly securing the head support to the imaging ring during an imaging procedure.

* * * * *